United States Patent [19]

Marinoff et al.

[11] Patent Number: 5,472,448

[45] Date of Patent: Dec. 5, 1995

[54] SURGICAL KNIFE BLADE HOLDER AND SUPPORT

[75] Inventors: Gerald P. Marinoff, New City; G. Lawrence Abrams, Fort Montgomery, both of N.Y.

[73] Assignee: G & G Medical Instruments Ltd., Fort Montgomery, N.Y.

[21] Appl. No.: 213,726

[22] Filed: Mar. 16, 1994

[51] Int. Cl.⁶ .................................................. A61B 17/16
[52] U.S. Cl. ............................................. 606/172; 30/276
[58] Field of Search ........................... 606/170, 171–172, 606/166

[56] References Cited

U.S. PATENT DOCUMENTS

| | | | |
|---|---|---|---|
| 5,195,533 | 3/1993 | Chin et al. | 606/170 X |
| 5,203,865 | 4/1993 | Siepser | 606/166 |
| 5,222,967 | 6/1993 | Casebeer et al. | 606/167 X |
| 5,304,191 | 4/1994 | Gosselin | 606/172 |
| 5,312,428 | 5/1994 | Lieberman | 606/166 |

*Primary Examiner*—Stephen C. Pellegrino
*Assistant Examiner*—Nancy Mulcare

[57] ABSTRACT

The surgical knife of the present invention includes a substantially cylindrical housing which has an external housing surface and one open end. A planar knife blade is support for axial movement within the housing so that one end of the knife blade can be extended beyond the open end of the housing. Means, which are well known in the art, are carried by the housing and connected to the knife blade to cause movement of the knife blade in an axial direction for extension beyond the open end. A raised surface is provided on the housing which has a cross section dissimilar to the cross section of the housing for use in preventing rotation of the knife to thereby orient the knife blade along a desired plane when the knife is supported on a surface. One embodiment of the surgical knife provides for the dissimilar cross section to be a square with four flat surfaces so that these surfaces can rest in a complimentary groove in a supporting tray of a knife blade setting device. A complimentary support tray is also provided to insure that the knife is properly oriented in a knife setting device when the housing is carried by the support tray.

8 Claims, 2 Drawing Sheets

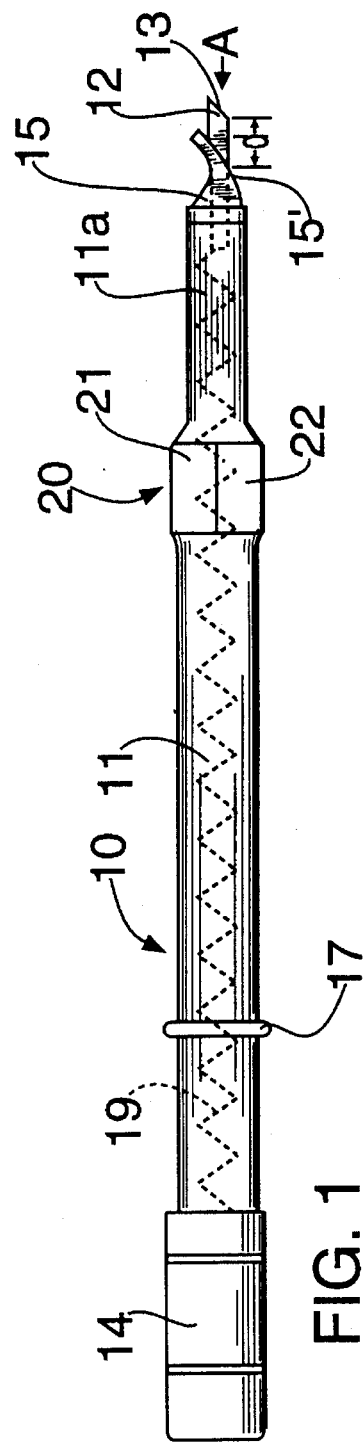
FIG. 1
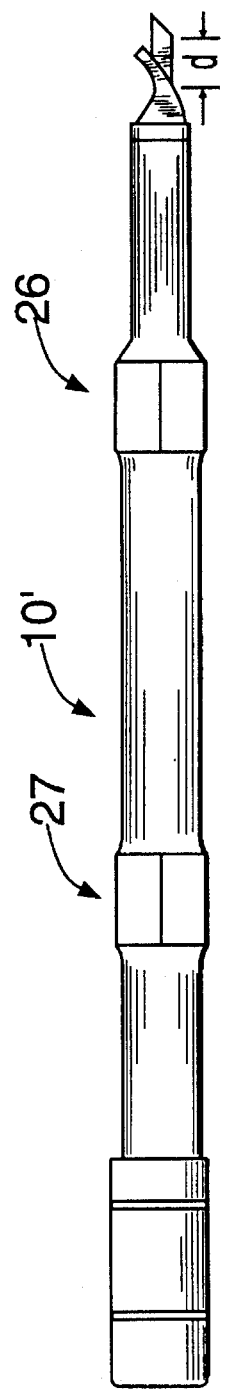
FIG. 2
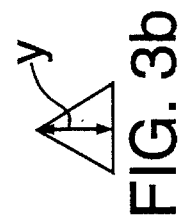
FIG. 3b
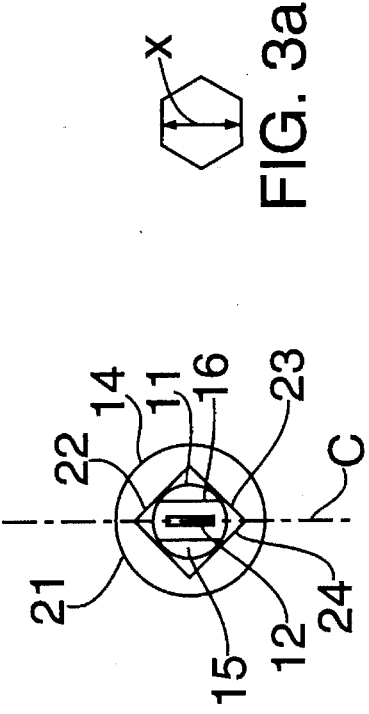
FIG. 3a
FIG. 3

SURGICAL KNIFE BLADE HOLDER AND SUPPORT

FIELD OF THE INVENTION

This invention relates generally to the field of surgical instruments and is more particularly directed to a hand held holder for a knife blade intended for use in ophthalmic surgical procedures, and a support for the holder used for setting the knife extension.

BACKGROUND OF THE INVENTION

Knife blade holders are well known and commonly used in ophthalmic surgery. The typical knife blade used in today's surgical procedures is usually constructed of diamond having a planar body with a cutting edge at one end. The blade is typically carried within a cylindrical housing with the cutting edge arranged so that it extends beyond one end of the cylindrical housing which has an opening to accommodate the blade. A mechanism is usually carried within the cylindrical housing and connected to the blade to permit axial movement of the blade with respect to the end of the cylindrical housing so that the blade can be totally withdrawn into the cylindrical housing when not in use and extended beyond the end thereof by a predetermined desired amount for use in surgical procedures.

For most ophthalmic surgical procedures, depth of incision is a critical factor in success of the procedure. The amount of extension of the cutting edge of the knife blade beyond the end of the cylindrical housing is a critical dimension for proper ophthalmic surgical procedures because it determines the depth of incision. Numerous devices have been developed and are in use to facilitate measuring the distance, and presetting the amount, of extension of the cutting edge of the knife blade beyond the open end of the cylindrical housing. One such device is illustrated and described in issued U.S. Pat. No. 4,662,075. In this prior art, the typical knife blade holder 14 carrying the knife blade 16 is illustrated. The device of this prior art provides a tray having a central groove 84 to support and accommodate the knife blade holder 16. The tray is moveable toward and away from a fixed plane, so that the blade holder can also be moved relative to the fixed plane. In this manner, the extension of the knife blade beyond the open end of the cylindrical housing can be set.

However, because the knife blade is planar, its cutting edge will also lie along a plane which must be properly oriented in the setting device in order to correctly adjust the extension of the blade beyond the end of the holder. The prior art holders do not provide any means to insure that the cutting edge will lie in a properly oriented plane (a vertical plane) when setting the edge extension.

It is accordingly a general object of the present invention to provide surgical knife blade holder and complimentary support tray to overcome the disadvantages of the prior art when setting the knife blade cutting edge.

It is also an object of the present invention to provide a knife blade holder which will insure proper alignment of the knife blade in a supporting tray when used to adjust and set the amount of extension of the knife blade cutting edge beyond the end of the cylindrical housing of the blade holder.

Another more specific object of the invention is to provide a knife blade holder which has means to orient the blade along the desired plane when placed in a blade setting device.

The above objects, features and advantages, along with other objects, features and advantages of the present invention will become more apparent from the detailed description of the invention in conjunction with the accompanying drawings to be described more fully hereinafter.

SUMMARY OF THE INVENTION

The present invention is directed to an improved surgical knife for use in ophthalmological surgical procedures.

The surgical knife of the present invention includes a substantially cylindrical housing which has an external housing surface and one open end. A planar knife blade is support for axial movement within the housing so that one end of the knife blade can be extended beyond the open end of the housing. Means, which are well known in the art, are carried by the housing and connected to the knife blade to cause movement of the knife blade in an axial direction for extension beyond the open end. A raised surface is provided on the housing which has a cross sectional shape dissimilar to the cross section of the housing for use in preventing rotational movement of the knife to thereby orient the knife blade along a desired plane when the knife is supported on a surface. One embodiment of the surgical knife provides for the dissimilar cross sectional shape to be a square with four flat surfaces arranged at 90° to each other so that these surfaces can rest in a complimentary groove in a supporting tray of a knife blade setting device. A complimentary support tray when used in combination with the housing insures proper orientation of the knife blade when the tray carrying the holder is used in a knife setting device.

The foregoing and other features of the present invention are more fully described with reference to the following drawings annexed hereto.

BRIEF DESCRIPTION OF THE DRAWINGS

FIG. 1 is a side view of a knife blade holder according to one embodiment of the present invention;

FIG. 2 is a similar side view of a knife blade holder illustrating an alternate embodiment of the present invention;

FIG. 3 is an end view of the embodiments of FIGS. 1 and 2 as seen along the direction of Arrow A;

FIGS. 3a and 3b are schematic illustrations of polygonal cross sectional shapes used in either of the embodiments of FIGS. 1 or 2;

DESCRIPTION OF THE INVENTION

Figure 4:
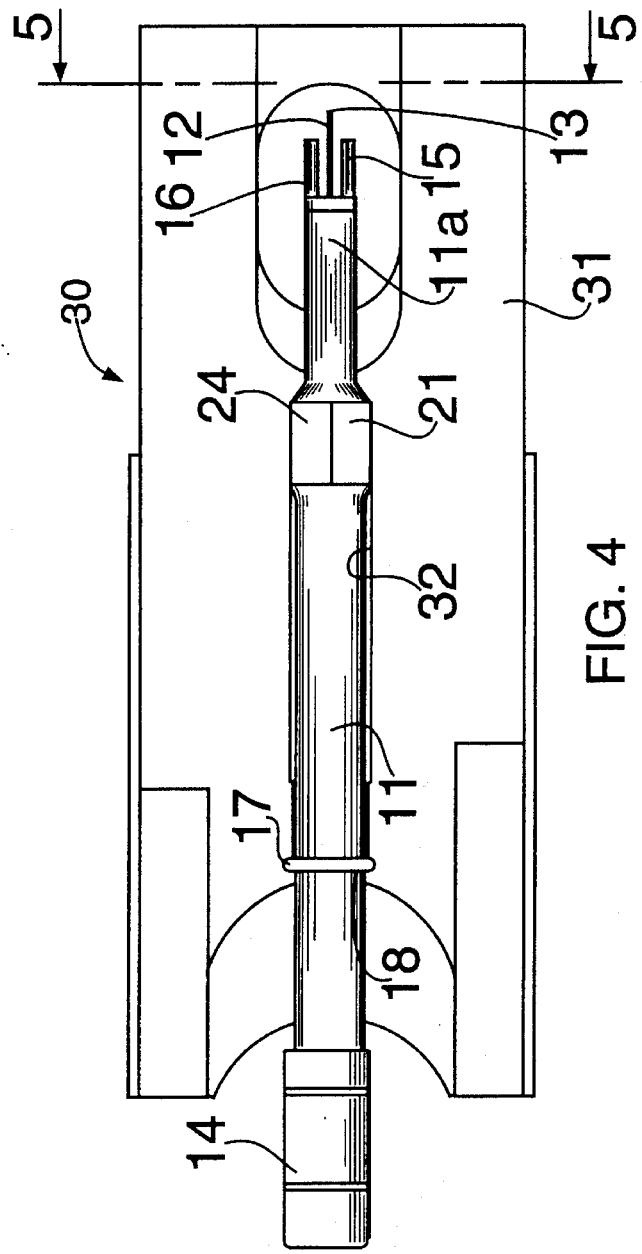
FIG. 4 is a plan view of the supporting tray of the present invention showing the knife blade holder of FIG. 1 in its supported position for use in the setting device such as illustrated in the prior art discussed above.

With reference to FIG. 1, a preferred embodiment of the knife holder of the present invention is illustrated. The surgical instrument 10 of this embodiment includes a cylindrical housing 11 forming the knife blade holder for the diamond knife 12 which has a cutting edge 13. The knife blade 12 lies in a plane C as shown in FIG. 3, and is connected to a mechanism (not shown in detail, but well known in the art) within the holder 11 for moving the blade in an axial direction with respect to the housing 11. In this manner, the blade can be extended in a direction opposite to arrow A, or can be completely withdrawn into the forward portion 11a of the housing. In a typical fashion, rotatable collar 14 is connected to a screw-type mechanism 19 (shown schematically in FIG. 1) within the housing which is connected to the blade 12, so that upon rotation of the collar 14 the blade 12 can be withdrawn into the holder 11a or extended beyond the holder into the position shown in either FIG. 1 or 2.

The instrument 10 is also provided with a pair of spaced apart feet 15 and 16 between which the blade 12 is arranged. The feet 15, 16 each have a heel portion 15', 16' which are used for resting on the surface of the eye when a surgeon uses the instrument. When the blade 12 is extended as shown in FIG. 1, by a distance—d—beyond the heel 15', 16', this will determine the depth of incision when the heel rests on the eye surface.

The instrument of the present invention is provided with a portion 20 having flattened surfaces to facilitate the placement of the blade holder onto the supporting tray in such a manner as to insure alignment of the blade 12 along the plane C. In the embodiment shown herein, there are four such flattened surfaces forming a raised square integral with the holder 11. The four flattened surfaces 21, 22, 23, 24 are each arranged at a 90° angle with respect to its adjacent flattened surface, and its sides are longer than the diameter of the housing. Numerous alternate arrangements can be envisioned in which the cross section of the flattened surfaces can be any polygonal shape. The important feature is to provide a surface dissimilar to the cylindrical body of the holder 11 in order to insure that the holder can be secured in the tray so that the blade 12 will lie along the desired plane. This requires that the distance between opposing flat surfaces "X" (see FIG. 3a) in a polygon having an even number of surfaces, or the distance "Y" between a flat surface of the polygon and its opposing angle, in a polygon having an odd number of surfaces (such as in FIG. 3b), is greater than the diameter of the cylindrical housing.

FIG. 2 illustrates an alternate embodiment of a surgical knife 10' in which two raised flattened areas 26 and 27 are provided. In all other respects, this embodiment is substantially identical to the embodiment of FIG. 1. In either embodiment of FIG. 1 or FIG. 2, the axial length of the flattened surfaces can be large relative to the overall length of the housing, but it is preferable that this length be less than about 25% of the length of the housing in order to provide a comfortable grip for the user.

Figure 5:
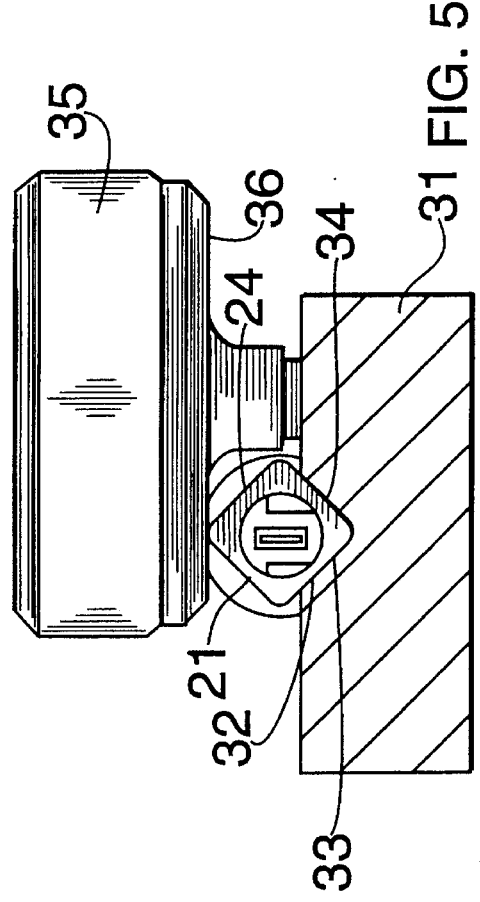
FIG. 5 is a sectional view taken along section lines B—B of FIG. 4.

With reference to FIGS. 4 and 5, the supporting tray 30 consists of a block 31 with a longitudinally extending groove 32. The groove has side walls 33 and 34 which are flat and oriented 90° with respect to each other. A knob 35 is mounted on the block 31 so that it may be screwed up or down. The knob has an undersurface 36 arranged to engage the blade holder. When the knob 35 is screwed down to engage the blade holder, the blade holder will be securely held in the longitudinal groove 32 and oriented in such a manner that the plane of blade 12 is fixed along plane C.

In the foregoing manner, the blade holder, securely held in tray 30 can be positioned for movement along a fixed base of a blade setting device, such as shown in the prior referenced patent, so that the blade can be appropriately adjusted for extension beyond the end of the feet 15, 16.

An additional feature is provided by flange 17 (see FIG. 1), which is preferably cylindrical but can be any cross sectional shape. When the flange 17 rests in a complimentary slot 18 in the tray 30, axial movement of the knife blade within the groove 32 will be prevented.

While the invention has been described and illustrated with respect to certain embodiments which produce satisfactory results, it will be understood by those skilled in the art, after understanding the purposes of the invention that various other changes and modifications may be made without departing from the spirit and scope of the invention, and it is, therefore, intended in the appended claims to cover all such changes and modifications.

What is claimed is:

1. An ophthalmological surgical knife comprising a substantially cylindrical housing having an external housing surface, and one open end, a planar knife blade carried by said housing axially moveable for extension beyond said open end, means carried by said housing connected to said blade for causing said movement, at least one surface area on said housing having a cross sectional shape dissimilar to the cross sectional shape of said cylindrical housing for preventing rotational movement of said housing in order to orient said knife blade along a desired plane when said knife is supported on a surface, a supporting tray for supporting said housing thereon when moving the knife blade relative to an end of said housing in order to set the extension thereof a predetermined distance beyond said open end, said supporting tray having a longitudinally extended groove having a cross sectional shape complimentary with the cross sectional shape of said surface area in order to prevent rotational movement of said knife blade within said groove when said knife blade is carried therein in order to orient said knife blade along a desired plane.

2. The ophthalmological surgical knife according to claim 1 wherein said cross sectional shape of said surface is polygonal when said cross section is taken transverse to the longitudinal access of said housing.

3. The ophthalmological surgical knife according to claim 2 wherein the distance between opposing sides of said polygon when said polygon has an even number of surfaces, and the distance between a side of said polygon and an opposing angle to said side when said polygon has an odd number of surfaces is greater than the diameter of said cylindrical housing.

4. The ophthalmological surgical knife according to claim 3 wherein said polygon is a square, the sides of said square being larger than the diameter of said cylindrical housing.

5. The ophthalmological surgical knife according to claim 4 wherein said surface area has an axial length less than 25% of the length of said housing.

6. The ophthalmological surgical knife according to claim 5 further comprising a second surface area having the same cross sectional shape as said first surface area, said surface areas each having an axial length less than 25% of the total length of said cylindrical housing.

7. The ophthalmological surgical knife according to claim 1 further comprising means carried by said housing for preventing axial movement of said housing when said housing is supported in said longitudinal groove.

8. The ophthalmological surgical knife according to claim 7 where said means for preventing axial movement comprises a flange carried by said housing and a complimentary slot in said tray for receiving said flange.

* * * * *